(12) United States Patent
Petty et al.

(10) Patent No.: US 9,962,160 B2
(45) Date of Patent: May 8, 2018

(54) SURGICAL STAPLERS WITH TISSUE PROTECTION AND RELATED METHODS

(71) Applicant: Wake Forest University Health Sciences, Winston-Salem, NC (US)

(72) Inventors: John K. Petty, Winston-Salem, NC (US); Lucas P. Neff, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 170 days.

(21) Appl. No.: 15/162,986

(22) Filed: May 24, 2016

(65) Prior Publication Data

US 2016/0262751 A1     Sep. 15, 2016

Related U.S. Application Data

(62) Division of application No. 13/410,760, filed on Mar. 2, 2012, now Pat. No. 9,370,362.

(Continued)

(51) Int. Cl.
*A61B 17/072*     (2006.01)
*A61B 17/068*     (2006.01)
(Continued)

(52) U.S. Cl.
CPC ...... *A61B 17/072* (2013.01); *A61B 17/00234* (2013.01); *A61B 17/068* (2013.01); *A61B 17/07207* (2013.01); *A61F 5/0086* (2013.01); *A61B 2017/00818* (2013.01); *A61B 2017/00827* (2013.01); *A61B 2017/07214* (2013.01); *A61B 2017/07228* (2013.01);
(Continued)

(58) Field of Classification Search
CPC ............ A61B 17/00234; A61B 17/072; A61B 17/07207; A61B 17/068; A61B 2017/07214; A61B 2017/07271; A61B 2017/07285; A61B 2017/00827; A61B 2017/00818; A61B 2017/306; A61F 5/0083; A61F 5/0086; A61F 5/0036
USPC ....... 606/139, 142, 143, 151, 153, 167, 213, 606/219, 192; 227/19, 176.1, 180.1
See application file for complete search history.

(56) References Cited

U.S. PATENT DOCUMENTS 4,354,628 A     10/1982   Green
4,610,383 A     9/1986    Rothfuss et al.
(Continued)

OTHER PUBLICATIONS

Adler, Richard H., Collis gastroplasty: Origin and evolution, The Annals of Thoracic Surgery, 1990, pp. 841-842, vol. 50.
(Continued)

*Primary Examiner* — Scott A. Smith
(74) *Attorney, Agent, or Firm* — Myers Bigel, P.A.

(57) ABSTRACT

Surgical staplers include: (a) a stapler head having opposed first and second elongate jaws with opposing proximal and distal end portions; (b) a staple cartridge held in at least one of the first and second jaws, the stapler cartridge configured to concurrently deliver a plurality of parallel rows of staples; and (c) a tissue protection segment held in a proximal portion of at least one of the first and second jaws. The jaws are configured to close against target tissue and, at stapler firing, staples are delivered to a subset of tissue held inside the jaws so that tissue held by the tissue protection segment adjacent the proximal end portion of the stapler is not stapled.

7 Claims, 10 Drawing Sheets

Related U.S. Application Data

(60) Provisional application No. 61/472,894, filed on Apr. 7, 2011.

(51) Int. Cl.
*A61B 17/00* (2006.01)
*A61F 5/00* (2006.01)
*A61B 17/32* (2006.01)
*A61B 90/00* (2016.01)

(52) U.S. Cl.
CPC .............. *A61B 2017/07271* (2013.01); *A61B 2017/07285* (2013.01); *A61B 2017/320052* (2013.01); *A61B 2090/061* (2016.02)

(56) References Cited

U.S. PATENT DOCUMENTS

| | | | |
|---|---|---|---|
| 4,788,978 A | 12/1988 | Strekopytov et al. | |
| 5,104,394 A | 4/1992 | Knoepfler | |
| 5,350,104 A | 9/1994 | Main et al. | |
| 5,397,324 A | 3/1995 | Carroll et al. | |
| 5,403,326 A * | 4/1995 | Harrison | A61B 17/0643 128/898 |
| 5,489,058 A | 2/1996 | Plyley et al. | |
| 5,571,116 A * | 11/1996 | Bolanos | A61B 17/07207 227/175.3 |
| 5,632,432 A | 5/1997 | Schulze et al. | |
| 5,655,698 A | 8/1997 | Yoon | |
| 5,658,300 A | 8/1997 | Bito et al. | |
| 5,749,893 A | 5/1998 | Vidal | |
| 5,833,695 A | 11/1998 | Yoon | |
| 5,868,760 A | 2/1999 | McGuckin, Jr. | |
| 6,010,054 A | 1/2000 | Johnson et al. | |
| 6,119,913 A | 9/2000 | Adams et al. | |
| 6,264,086 B1 | 7/2001 | McGuckin, Jr. | |
| 6,443,973 B1 | 9/2002 | Whitman | |
| 6,716,232 B1 | 4/2004 | Vidal et al. | |
| 6,755,338 B2 | 6/2004 | Hahnen et al. | |
| 6,769,590 B2 | 8/2004 | Vresh et al. | |
| 6,835,200 B2 * | 12/2004 | Laufer | A61B 17/0401 606/139 |
| 7,134,587 B2 | 11/2006 | Schwemberger et al. | |
| 7,287,682 B1 | 10/2007 | Ezzat et al. | |
| 7,407,076 B2 | 8/2008 | Racenet et al. | |
| 7,743,960 B2 | 6/2010 | Whitman et al. | |
| 7,909,220 B2 | 3/2011 | Viola | |
| 8,028,882 B2 | 10/2011 | Viola | |
| 8,028,884 B2 | 10/2011 | Sniffin et al. | |
| 8,083,120 B2 | 12/2011 | Shelton, IV et al. | |
| 8,276,801 B2 | 10/2012 | Zemlok et al. | |
| 9,370,362 B2 * | 6/2016 | Petty | A61B 17/072 |
| 2003/0120289 A1 * | 6/2003 | McGuckin, Jr. | A61B 17/072 606/151 |
| 2003/0132267 A1 * | 7/2003 | Adams | A61B 17/072 227/176.1 |
| 2004/0092974 A1 * | 5/2004 | Gannoe | A61B 17/072 606/153 |
| 2004/0094597 A1 | 5/2004 | Whitman et al. | |
| 2005/0038415 A1 * | 2/2005 | Rohr | A61F 5/0003 604/891.1 |
| 2005/0080438 A1 * | 4/2005 | Weller | A61B 17/07207 606/153 |
| 2005/0203547 A1 | 9/2005 | Weller et al. | |
| 2005/0256533 A1 * | 11/2005 | Roth | A61F 5/0083 606/167 |
| 2006/0151568 A1 * | 7/2006 | Weller | A61B 17/0218 227/175.1 |
| 2007/0167960 A1 * | 7/2007 | Roth | A61B 17/0218 606/153 |
| 2007/0233161 A1 | 10/2007 | Weller et al. | |

OTHER PUBLICATIONS

Armour, John, A Lesser Curvature Gastroplasty, The Canadian Medical Associated Journal, 1930, pp. 756-761.

Cameron et al., The Uncut Collis-Nissen Fundoplication: Results for 79 Consecutively Treated High-Risk Children, Journal of Pediatric Surgery, 1997, pp. 887-891, vol. 32, No. 6.

Durante et al., Verticla gastric plication versus Nissen fundoplication in the treatment of gastroesphageal reflux in children with cerebral palsy, Sao Paulo Medical Journal, 2007, pp. 15-21, vol. 125, No. 1.

Minjarez et al., Surgical therapy for gastroesophageal reflux disease, GI Motility online, 2006, 44 pages, http://www.nature.com/gimo/contents/pt1/full/gimo56.html.

Mutaf et al., Treatment of Gastroesophageal Reflux With a Gastric Tube Cardioplasty, Journal of Pediatric Surgery, Apr. 2003, pp. 571-574, vol. 38, No. 4.

Horvath et al., The Short Esophagus: Pathophysiology, Incidence, Presentation, and Treatment in the Era of Laproscopic Antireflux Surgery, Annals of Surgery, 2000, pp. 630-640, vol. 232, No. 5.

Taylor et al., Vertical gastric plication: an operation for gastro-oesophageal reflux, Annals of the Royal College of Surgeons of England, 1989, pp. 31-36, vol. 71.

Endo GIA™ Ultra Universal Stapler, Covidien Surgical, date unknown but assumed prior to Apr. 7, 2011, Printed from the internet on Mar. 7, 2012, 1 page, http://www.autosuture.com/autosuture/pageBuilder.aspx?topicID=194008&breadcrumbs=0:63659,39868:0,39870:0.

DST Series™ GIA™ Single Use Reloadable Stapler, Covidien Surgical, date unknown but assumed prior to Apr. 7, 2011, Printed from the internet on Mar. 7, 2012, 1 page, http://www.autosuture.com/autosuture/pageBuilder.aspx?topicID=234&breadcrumbs=0:63659,39868:0,39872:0.

Echelon Flex™ 60 Endopath® Stapler, Ethicon Endo-Surgery, date unknown but assumed prior to Apr. 7, 2011, Printed from the internet on Mar. 7, 2012, 1 page, http://www.ethiconendosurgery.com/Clinician/Product/stapling/echelonflexendocutter#description-specs.

Proximate® Linear Cutters, Ethicon Endo-Surgery, date unknown but assumed prior to Apr. 7, 2011, Printed from the internet on Mar. 7, 2012, 1 page, http://www.ethiconendosurgery.com/Clinician/Product/stapling/etsarticulatingendocutter#description-specs.

Endopath® ETS Articulating Linear Cutters, Ethicon Endo-Surgery, date unknown but assumed prior to Apr. 7, 2011, Printed from the internet on Mar. 7, 2012, 1 page, http://www.ethiconendosurgery.com/Clinician/Product/stapling/linearcutters#description-specs.

\* cited by examiner

SURGICAL STAPLERS WITH TISSUE PROTECTION AND RELATED METHODS

RELATED APPLICATIONS

This application is a divisional application of U.S. patent application Ser. No. 13/410,760, filed Mar. 2, 2012, now U.S. Pat. No. 9,370,362, which claims the benefit of and priority to U.S. Provisional Application Ser. No. 61/472,894 filed Apr. 7, 2011, the contents of which are hereby incorporated by reference as if recited in full herein.

FIELD OF THE INVENTION

This invention relates to surgical staplers that may be particularly useful for gastrointestinal surgeries.

BACKGROUND OF THE INVENTION

Gastroesophageal reflux disease (GERD) can occur in children. Unfortunately, some of these children have such severe GERD that it cannot be managed with medication. These children may benefit from anti-reflux surgery. Neurologically impaired (NI) children may have a severe form of GERD with emetic reflux. The standard anti-reflux surgery, Nissen Fundoplication (NF), is less effective in NI children and NI treatment can lead to other complications and a relatively high failure rate. An alternative anti-reflux surgery, gastroplasty with restricted antrum to control emesis (GRACE), has been developed in an animal model. This surgery can be more effective than NI in controlling reflux emesis.

Known surgical staplers are used to deploy at least two parallel rows of staples from a proximal end of the jaws of the staplers to the distal end. A knife blade can divide the tissue between two adjacent rows to provide a stapled division of tissue. However, conventional staplers are not suitably configured to safely and/or optimally perform the GRACE procedure.

SUMMARY OF EMBODIMENTS OF THE INVENTION

Embodiments of the present invention are directed to surgical staplers that can be used to perform a GRACE procedure.

Embodiments of the present invention are directed to surgical staplers with a proximal tissue protection segment.

Some embodiments are directed to surgical staplers that include: (a) a stapler head having opposed first and second elongate jaws with opposing proximal and distal end portions; (b) a staple cartridge held in at least one of the first and second jaws, the stapler cartridge configured to concurrently deliver a plurality of parallel rows of staples; and (c) a tissue protection segment held in a proximal portion of at least one of the first and second jaws. The jaws are configured to close against target tissue and, at stapler firing, staples are delivered to a subset of tissue held inside the jaws so that tissue held by the tissue protection segment adjacent the proximal end portion of the stapler is not stapled.

The staples in the cartridge can be held longitudinally spaced apart from the tissue protection segment (closer to the distal end portion of the respective jaw).

The tissue protection segment can be formed by or held in the stapler cartridge.

The tissue protection segment can be defined by at least one inner surface of the first and/or second jaw of the stapler head.

The jaws can have a straight configuration. At least one of the jaws can have an arched leading edge portion.

The tissue protection segment can be configured as an interior facing recess configured to inhibit tissue crushing for tissue held thereat when the jaws close.

The tissue protection segment can include at least one resilient member configured to translate transversely outward in a direction substantially orthogonal to a longitudinally extending centerline of a shaft of the stapler when the jaws close against tissue to thereby inhibit tissue crushing for tissue held thereat when the jaws close.

The tissue protection segment can have a length that is between about 10-30 mm.

The active stapling portion of the stapler cartridge can have a length that is between about 30-80 mm.

The stapler may optionally also include a cutting member configured to extend and retract from one of the first or second jaws. The cutting member can be configured to cut only tissue proximate the stapled tissue held against the staple cartridge.

The cutting member can be configured to pivotably translate upward or downward to be aligned with an axially extending centerline of the stapler head to cut tissue between two adjacent stapled rows of tissue.

The tissue protection segment can include a scalloped interior-facing surface.

In some embodiments, when the jaws close against target tissue held by the tissue protection segment adjacent the proximal end portion of the stapler, the tissue threat is held snugly without introducing undue compressive injury.

In some embodiments, the stapler head can be configured to releasably interchangeably hold a first stapler cartridge that includes the tissue protection segment and a second stapler cartridge that is devoid of the tissue protection segment.

The stapler may optionally include a circuit configured to direct the stapler to operate in a tissue protection mode or in a full length stapling mode. The circuit can be in communication with a staple drive mechanism that delivers the staples from the staple cartridge. In the tissue protection mode, the stapler cartridge delivers staples only from a distal to medial portion of the stapler head. In the full length stapling mode, the staple cartridge delivers staples from the proximal portion of the stapler head as well as the distal and medial portions.

Other embodiments are directed to gastrointestinal treatments. The treatments can include: (a) providing a stapler with a staple head having first and second opposed jaws, with at least one of the jaws having a tissue protection segment proximate a staple cartridge; (b) inserting the stapler into a patient in an inferior to superior direction so that one jaw resides over one outer wall of the stomach and the other jaw resides under an opposing outer wall of the stomach; (c) closing the jaws against the stomach whereby an inferior portion of the stomach is held in the tissue protection portion of the stapler head and a more superior portion of the stomach is held against the stapler cartridge, wherein tissue held against the tissue protection segment is protected from undue (compressive) injury; then (d) applying a plurality of parallel rows of staples to only the more superior portion of the stomach and not to tissue held in the tissue protection segment of the stapler jaws; and (e) cutting between two adjacent rows of stapled tissue to divide the stomach tissue.

The applying and cutting steps can be carried out to form a first opening through the stomach with a stapled perimeter of tissue.

The method can also include applying staples to additional tissue above the first opening in a length sufficient to reach a junction of a natural esophagus at an upper portion of the stomach; and cutting the additional stapled tissue to form a neo-esophagus. The method may also include using a lower portion of the stapled tissue of the first opening to form part of a base portion of a neo-esophagus and/or an upper wall of a junction merging with a common channel.

Other embodiments are directed to methods of applying staples to a limited region of tissue. The methods include: (a) inserting a surgical stapler into a patient, the surgical stapler having first and second cooperating opposed jaws; (b) closing the jaws about a target region of tissue; then (c) applying a plurality of rows of staples to a first sub-portion of tissue held between the jaws while protecting a second sub-portion of tissue from compressive injury; and (d) cutting between two adjacent parallel rows of applied staples to form an opening with a stapled perimeter of divided tissue that is spaced apart from but proximate the second sub-portion of tissue.

The tissue can include stomach tissue and/or esophageal tissue.

Yet other embodiments are directed to a computer program product for bimodal operation of a surgical stapler. The computer program product includes a non-transitory computer readable storage medium having computer readable program code embodied in the medium. The computer-readable program code includes (a) computer readable program code that allows a user to select whether to operate in a full staple mode or in a tissue protection mode; and (b) computer readable program code that communicates with a loaded staple cartridge and/or a staple drive mechanism to selectively deliver a full length of staples in the full staple mode or a subset of a length of staples in the tissue protection mode.

Embodiments of the present invention are directed to surgical staplers that allow limited cutting only between staple lines.

The foregoing and other objects and aspects of the present invention are explained in detail in the specification set forth below.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DESCRIPTION OF EMBODIMENTS OF THE INVENTION

Figure 1:
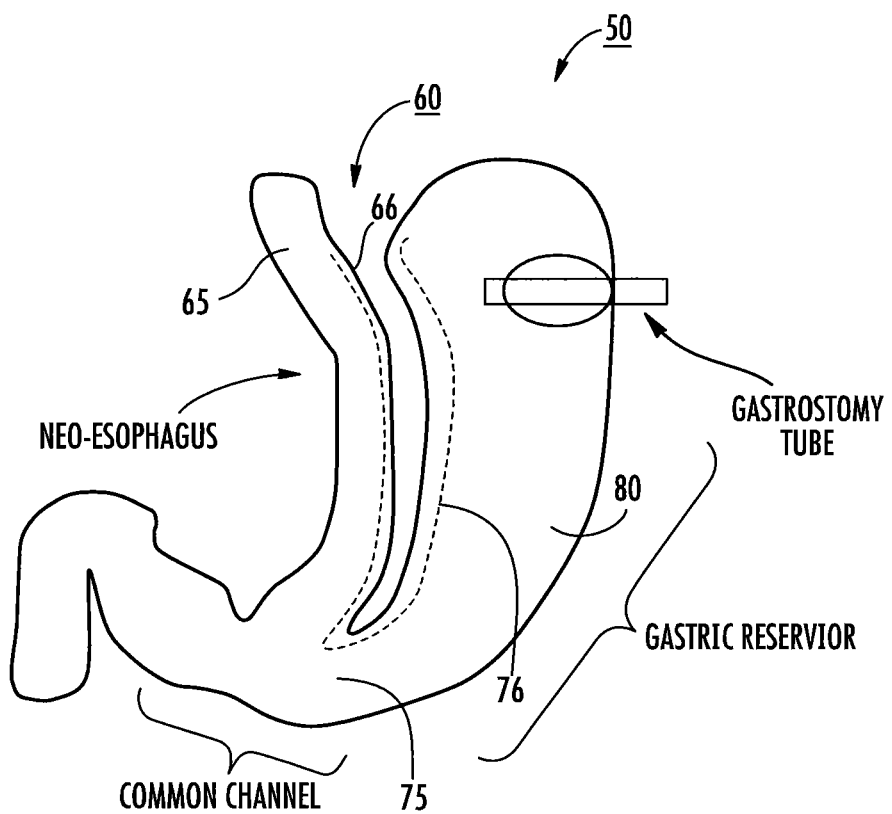
FIG. 1 is a schematic illustration of a GRACE procedure illustrating a divided division of tissue.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

The term "staple cartridge" refers to a device that holds a plurality of staples in alignment for attaching to tissue of a subject (e.g., patient) using a surgical stapler. The staple cartridge can be formed to be integral with or releasably attached to one or both of the opposed jaw(s) of the stapler.

The term "scalloped" refers to a surface with at least one notched or recessed region in an interior, tissue-contacting wall or surface of the stapler, and may include a series of notches or projections, including, for example, semi-circularly curved projections, that contacts tissue without introducing undue compressive injury when the stapler is closed and "fired".

The term "firing" and derivatives thereof refers to activation of the stapler to discharge staples.

The term "undue injury" means that the tissue held by the jaws at the tissue protection segment may have some (minor) compressive injury but that the tissue will still function and/or return to a substantially normal status post-surgery.

Embodiments of the invention are useful for veterinarian and human uses as well as for animal studies. That is, methods and devices provided by embodiments of the invention can be configured for any species of interest, e.g., mammalian including human, simian, murine, rat, lagomorph, bovine, ovine, caprine, porcine, equine, feline, canine, and the like.

Turning to FIG. 1, a post-GRACE configuration of a subject's stomach is shown. This procedure creates a staple line 66, 76 from inferior to superior, as that is the position of the surgeon relative to the gastro-esophageal junction 60 for anti-reflux surgery. The final stapled division of stomach tissue forms a neo-esophagus 65, a common channel 75, and the gastric reservoir 80 (e.g., reconfigured stomach).

Figure 2A:
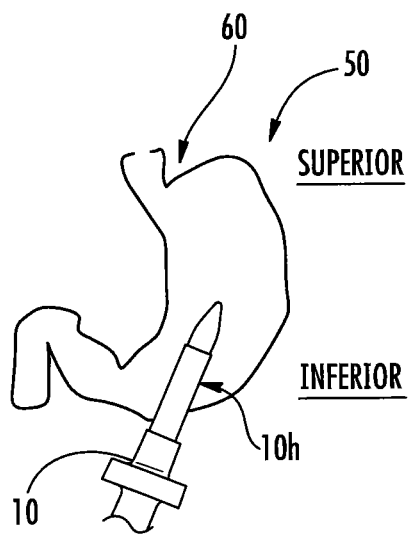
FIGS. 2A-2D illustrate a sequence of operations that can be used to perform the GRACE procedure according to embodiments of the present invention.
Figure 2B:
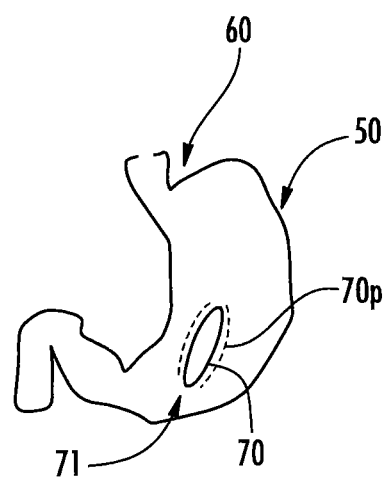

FIGS. 2A-2D illustrate a sequence of stapling to carry out the GRACE procedure. FIGS. 2A and 2B illustrate a first staple delivery step to form a first divided tissue segment 70. A surgical stapler 10 is placed about an inferior (lower) segment of the stomach and is configured to place staples through an inferior (lower) portion of the stomach. Notably, the surgical stapler 10 is configured to avoid injuring the most inferior tissue of the stomach 71 to leave a substantially undisturbed common channel 75 of stomach for feedings (FIG. 1). As will be discussed further below, the stapler 10 has a tissue protection segment 20 (FIGS. 2, 3) that resides adjacent a staple cartridge 30 (FIGS. 2, 3) that allows (a) at least two substantially parallel linear rows of staples to be applied to the stomach while the staple head 10h concurrently closes against the most inferior tissue of the stomach 71 but leaves this tissue substantially undisturbed or, at least, without undue injury, so that it can function to provide the common channel 75.

The stapler 10 can also include a cutting member 40 such as a knife, blade, heat, or other cutting means including a laser, RF energy and combinations thereof, that cuts the tissue only between two adjacent rows of stapled tissue (typically associated with only a forward and medial portion of the stapler head). The cutting of the stapled tissue divides the tissue and forms a stapled, substantially oblong or oval perimeter 70p (the applied staples are represented by the broken line about the perimeter of the tissue opening) about the opening 70 formed in the stomach (FIG. 2B).

FIGS. 2A and 2B illustrate that a first stapler 10 can be used to form the initial tissue division 70. This tissue division can be formed using a single "firing" of the stapler 10. That is, the staple cartridge 30 can have sufficient numbers of staples (with staple delivery channels and opposing anvils) to provide the desired tissue division length that can be applied concurrently with one activation of the stapler 10.

Figure 2C:
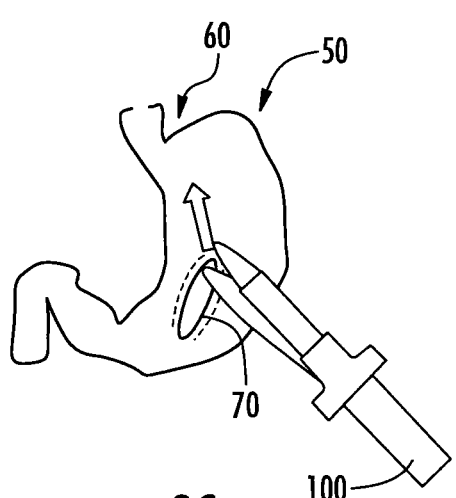
Figure 2D:
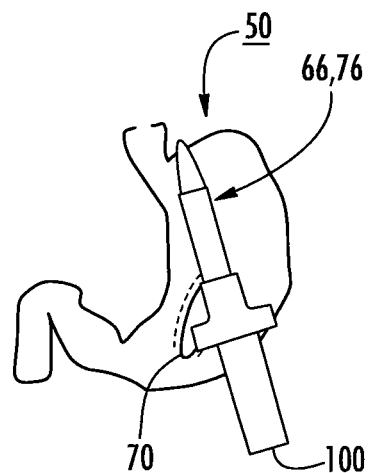

FIGS. 2C and 2D illustrate that a different (e.g., conventional linear array) stapler 100 can be used to complete the tissue division of the stomach above the first opening 70. Examples of conventional staplers that may be suitable for this use include, for example, staplers commercially available from Covidien (Autosuture) including Endio GIA™ Ultra Universal Stapler, MultiFire Endo GIA™ 30 Stapler, and MultiFire GIA™ Single Use Reloadable Stapler. Additional examples of conventional staplers that may be suitable for this use include, for example, staplers commercially available from Johnson & Johnson (Ethicon) including, but not limited to, Echelon™ 45 mm Endocutters, ETS Flex 45 mm EndocuttersCTS45, and the Proximate® Linear Cutter. These types and other types of surgical staplers may also be modified to have the tissue protection segment 20 (the tissue protection segment is discussed further below, see, for example, FIGS. 3 and 4).

It is also noted that in some embodiments, the same stapler 10 can be used to complete the tissue division using a plurality of successive firings and movement of the stapler to staple the remaining tissue. Thus, embodiments of the invention do not require a separate stapler. Further, the stapler 10 can include an integral cutting member or a separate cutting member can be used. It is also noted that the stapler 10 can be a single use disposable stapler.

It is contemplated that the stapler 10 and, where used, stapler 100 can be configured to perform similar to high-performance staplers to deliver two or three rows of parallel staples on each side of the divided staple line, a staple height (and/or height to crown or leg width ratio or aspect) appropriate for the thickness of tissue, and uncut rows of staples at the most distal aspect of the staple line if additional firings of the stapler are needed to extend the staple line. The stapler 10 can be configured to create a divided staple line from the middle and distal portions of the stapler head while preserving the tissue in the proximal portion of the stapler head.

Figure 3:
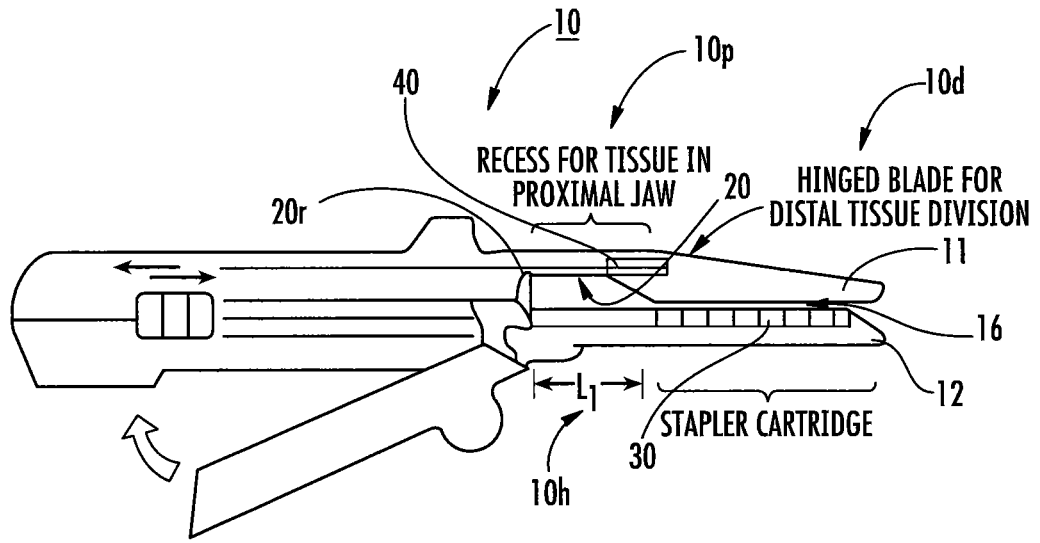
FIG. 3 is a side view of an exemplary surgical stapler according to embodiments of the present invention.

FIG. 3 illustrates an embodiment of the stapler 10. As shown, the stapler head 10h includes a pair of opposing jaws 11, 12. The staple cartridge 30 can be held in the lower jaw 12 as shown. The upper jaw 11 can include an anvil surface 16 that cooperates with the staples from the lower jaw 12 to bend and/or deform the legs of staples to staple tissue (which resides between the upper and lower jaws 11, 12 during stapling). However, the stapler 10 can alternatively be configured with the stapler cartridge 30 in the upper jaw 11 and the anvil surface in the lower jaw. In yet another alternative, both the upper and lower jaws 11, 12, respectively, may include staple cartridges 30 and anvil surfaces 16, with staples offset from each other (not shown). For an example of surgical staplers with staples and anvils held in both jaws, see U.S. Pat. No. 5,655,698, the contents of which are hereby incorporated by reference as if recited in full herein.

The stapler 10 can be a linear stapler with the jaws 11, 12 being substantially straight and substantially in-line with a staple shaft body upstream of the distal stapler head 10h above a handle 13 as shown, for example, in FIGS. 3, 4, 5, 12B and 12C. The handle 13, where used, is typically at a proximal end of the shaft 14 while the stapler head is at the distal end of the shaft as shown in FIG. 6. The jaws 11, 12, when closed, can be substantially parallel to and/or axially aligned with a centerline of a shaft extending from the staple head 10h. However, the jaws 11, 12 may alternatively have a curvature. Again, see U.S. Pat. No. 5,655,698 for an example of a curved surgical stapler head, the contents of which are again incorporated by reference.

Figure 4:
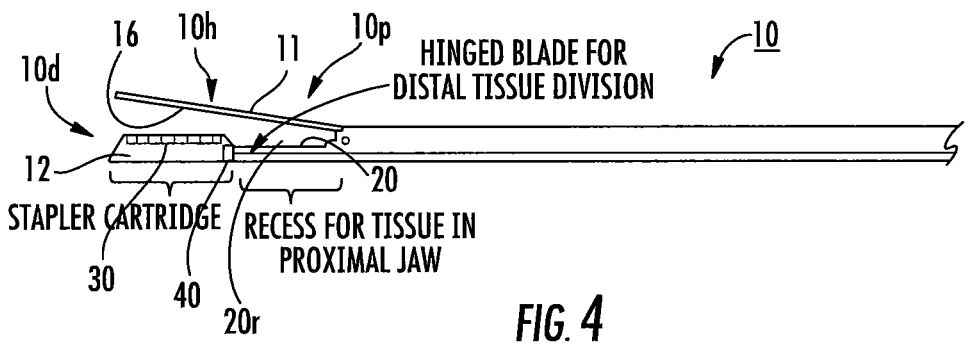
FIG. 4 is a side view of an exemplary surgical stapler according to other embodiments of the present invention.

Referring to FIGS. 3 and 4, the stapler 10 can include a tissue protection segment 20 that resides in the "heel" portion of the stapler head 10h between the jaw hinge and the stapler cartridge 30. The tissue protection segment 20 can be configured in a number of ways that allows the stapler jaws 11, 12 to close against target tissue without unduly compressing and/or injuring that tissue and without applying staples to this tissue. This configuration of the stapler head 10h allows for proximal protection of tissue with concurrent distal stapling of tissue.

In some embodiments, the stapler cartridge 30 can extend under or over the tissue protection segment and indeed, may be configured to provide the tissue protection segment 20, but is configured so as to not to deliver staples to tissue held in the tissue protection segment, e.g., no staples are loaded into these delivery passages and/or staples are not "fired" from a rear portion of the cartridge 30 for the initial firing or when tissue protection is desired.

The tissue protection segment 20 can have a length $L_1$ that corresponds to the tissue that is desirous of protection; for the GRACE procedure, the length is typically between about 10 mm to about 30 mm, typically about 20 mm. Depending on a particular target region, and according to some particular embodiments, the tissue protection can be sized to accommodate between about 30 mm to about 100 mm in tissue thickness, typically between about 30 mm to about 75 mm in tissue thickness, and more typically between about 30 mm to about 50 mm, without causing undue compressive injury to the tissue held thereat.

The stapler cartridge 30 can have a length $L_2$ that is about the same, greater or lesser than the length $L_1$. In some embodiments, the stapler cartridge 30 includes the tissue protection segment 20 and the staple delivery or "firing" part of the cartridge 30 has the length $L_2$. In some embodiments, the length $L_2$ is greater than the length $L_1$ by at least about 10%. The length $L_2$ is typically between about 30 mm to about 80 mm, typically about 40 mm, but noting this can vary depending on size of a pediatric or adult patient. In some embodiments, the stapler 10 can be provided in different sizes to accommodate various size patients, e.g., XS, S, M, L, XL and the like, that varies for one or both of the length of the tissue protection segment 20 and the length of the cartridge 30.

Further, although particularly suitable for lengthening the intra-abdominal esophagus and/or GRACE procedures, the stapler 10 may be useful for other surgeries including, for example, Collis Gastroplasty for treating esophageal cancer, bariatric surgery including, for example, the Magenstrasse and Mill procedure, esophageal lengthening procedures for clinical conditions such as esophageal atresia, caustic injury or resection for malignancy and the like. The lengths of the tissue protection segment 20 and/or staple cartridge 30 (for active staple delivery) can be adjusted accordingly.

As shown in FIG. 3, the upper jaw 11 includes the tissue protection segment 20. In this embodiment, the segment 20 comprises a recess 20r. FIG. 4 shows that the tissue protection segment 20 can be in the lower jaw 12. In this embodiment, the tissue protection segment 20 can also be a recess 20r. In other embodiments, the upper and lower jaws 11, 12 can each have cooperating tissue protection segments 20. In particular embodiments, the recess 20r and/or scallop 20s can have a depth of between about 30-100 mm. The tissue protection segment 20 resides closer to the proximal end portion of the stapler head 10p while the stapler cartridge 30 resides to closer the distal end portion of the stapler head 10d.

Figure 5A:
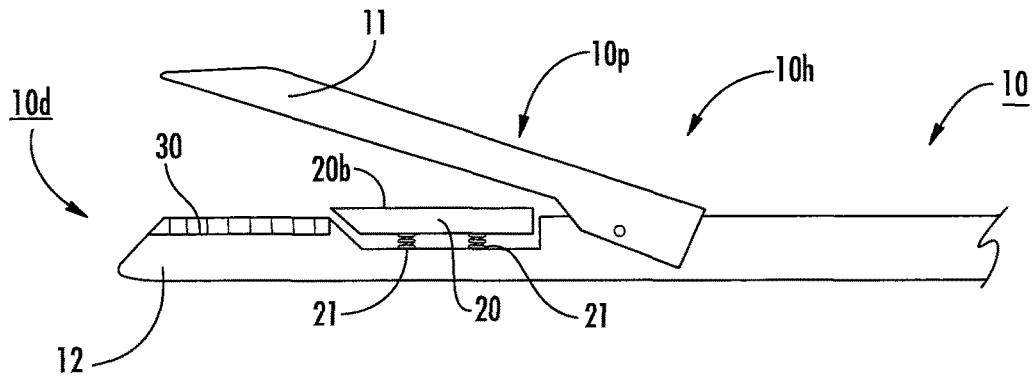
FIGS. 5A-5C are schematic illustrations of stapler heads with internal tissue protection segments according to embodiments of the present invention.
Figure 5B:
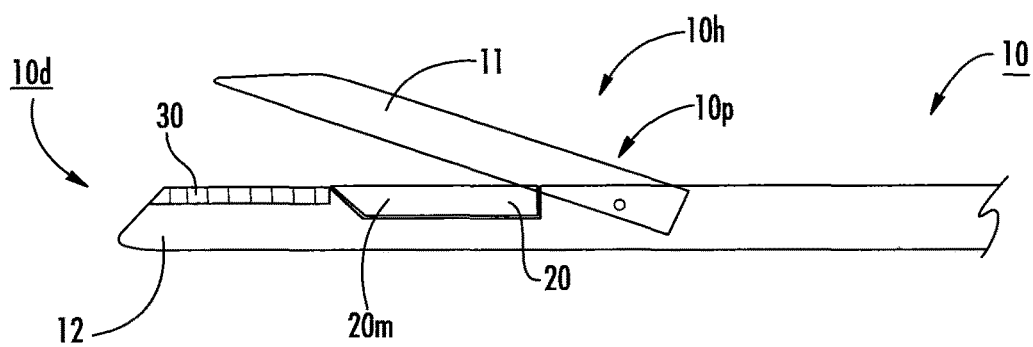
Figure 5C:
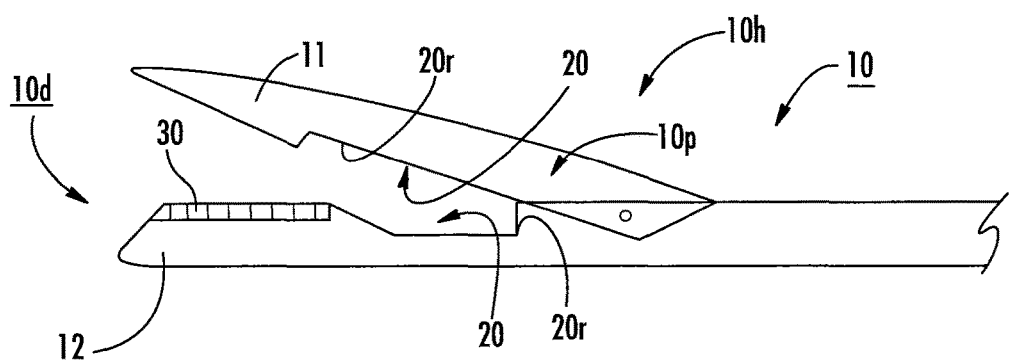
Figure 6:
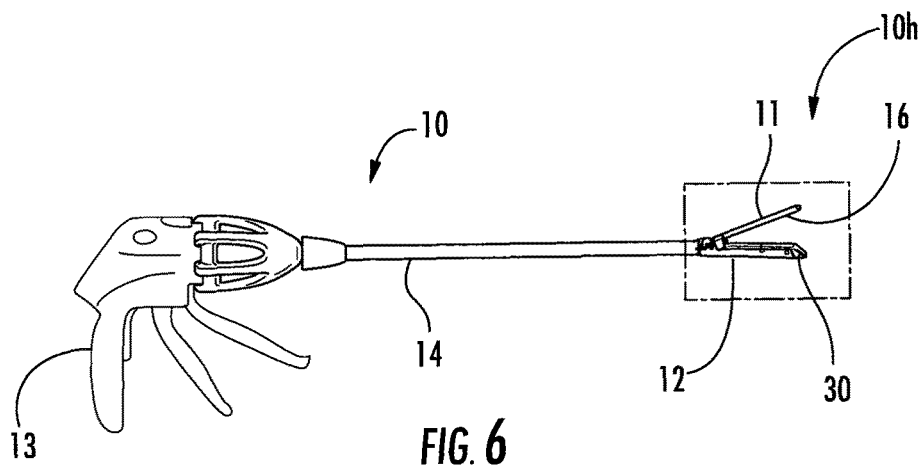
FIG. 6 is a side view of an exemplary laparoscopic stapler according to embodiments of the present invention.

FIGS. 5A-5C illustrate other examples of tissue protection segments 20. FIG. 5A illustrates that the tissue protection segment can include a block 20b in communication with one or more resilient members 21 that allows the block 20b to float or move downward, typically in a channel. When tissue for protection compresses against the block 20b, the block 20b is able to move down. The one or more resilient members 21 can comprise springs, washers, O-rings, elastomeric members and the like. The tissue protection segment 20 can include the block 20b placed in the upper jaw 11 rather than the lower jaw or in each jaw (not shown). The block 20b can comprise a biocompatible material (particularly the tissue contacting surface) such as metal (e.g., stainless steel), ceramic, polymeric and the like.

FIG. 5B illustrates the tissue protection segment 20 can include one or more resilient members 20m that is configured to compress inward to protect overlying tissue (or underlying tissue, if placed on the top jaw 11). The resilient member 20m can have a block-like shape. The member 24 can have a portion that is more resilient than another or a sub-portion that is resilient and a lower portion that is rigid. The resilient member 20m can comprise a monolithic body of a biocompatible flexible polymeric material. The tissue protection segment resilient member 20m can be placed in the upper jaw 11 rather than the lower jaw or in each jaw (not shown).

FIG. 5C illustrates that the tissue protection segment 20 includes top and bottom recesses 20r.

It is also contemplated that combinations of the tissue protection segments 20 described herein as well as other tissue protection segments may be used.

FIG. 6 illustrates that the stapler 10 can be a handheld laparoscopic stapler. However, the stapler 10 may also be useful for other types of staplers, including robotic surgery and more invasive surgeries (e.g., open surgical platforms).

Figure 7:
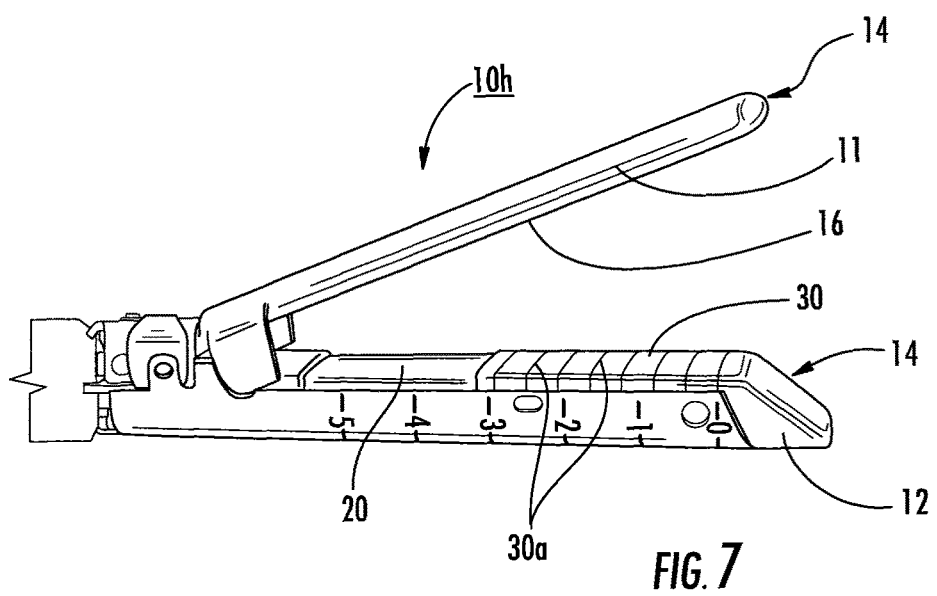
FIG. 7 is a side perspective view of a stapler head according to embodiments of the present invention.

FIG. 7 illustrates that the stapler head 10h can have a staple portion 30 that has a substantially flat surface with arrays of staple delivery apertures 30a that provide at least two (typically linear) parallel rows of staples to tissue. FIG. 7 also illustrates that the stapler head 10h can have a substantially arch-shaped front or leading edge 14 on either or both jaws 11, 12 that allows placement of the staples at a target superior portion of the stomach without applying pressure on an inferior part of the stomach, accessing from an inferior to superior position.

Figure 8:
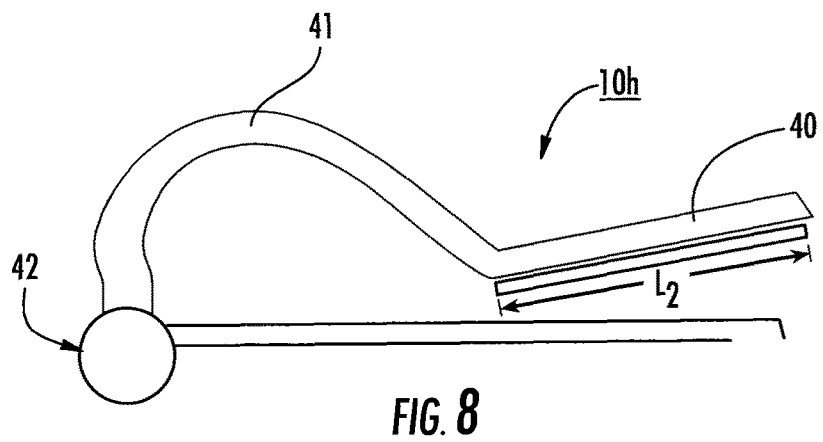
FIG. 8 is a side schematic illustration of a stapler head with a hinged cutting knife according to embodiments of the present invention.

FIG. 8 illustrates that the stapler head 10h can include a cutting member 40 (such as a knife or blade) positioned to reside over only the cutting cartridge 30 to cut tissue only where staples have been applied, between two adjacent rows of the stapled tissue lines. In some embodiments, as shown in FIG. 8, the cutting member 40 is pivotably attached to the stapler head 10h via a curved extension 41 and hinge 42 that resides upstream of the tissue protection segment 20.

Figure 9:
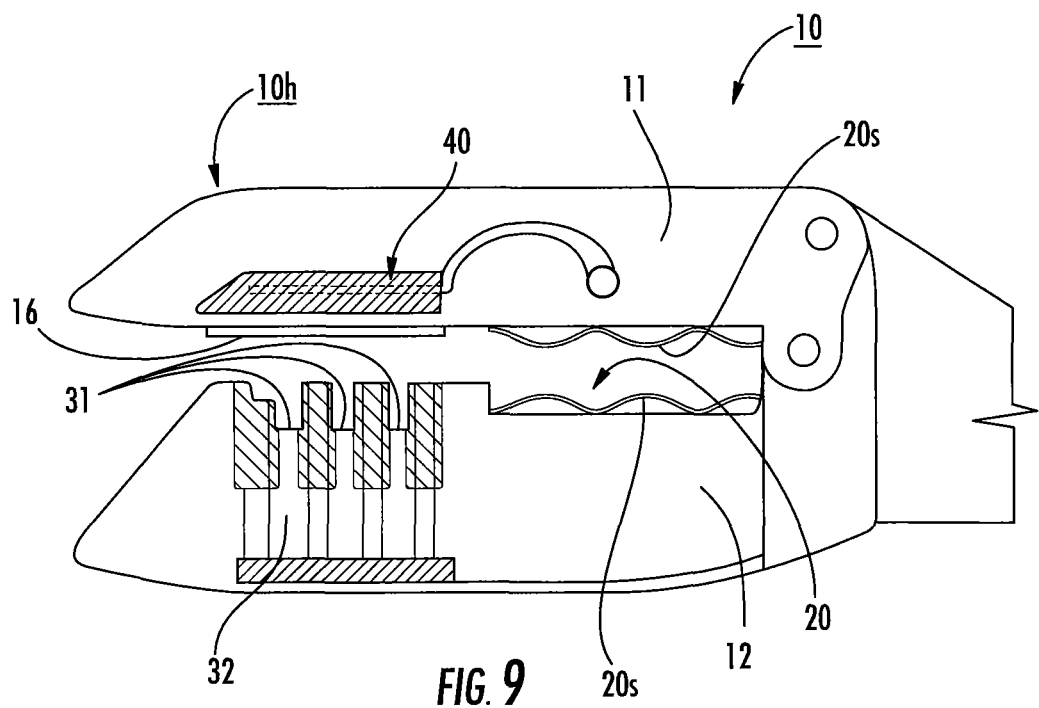
FIG. 9 is an enlarged side partial cutaway view of a stapler head according to embodiments of the present invention.

FIG. 9 illustrates that the tissue protection segment 20 can include a scalloped surface 20s. The scalloped (or notched) surface 20s defines a zone of substantially uncompressed (or minimally compressed) tissue when the stapler is closed and fired. FIG. 9 also illustrates (schematically) staples 31 in staple exit paths 32 ready for discharge from the cartridge 30 during "firing" of the stapler 10. In addition, FIG. 9 illustrates the cutting member 40 configured to extend out of the respective jaw 11 (shown as in the upper jaw but the cutting member 40 may alternatively be in the lower jaw 12) to cut only the tissue corresponding to the forward part of the stapler head 10h associated with the cartridge 30.

Figure 10:
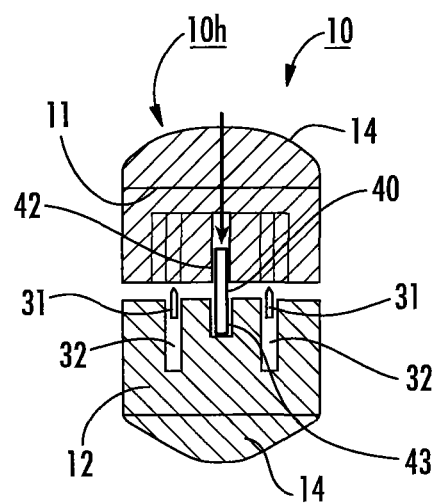
FIG. 10 is a lateral section view of a stapler head according to some embodiments of the present invention.

FIG. 10 illustrates the cutting member 40 held in aligned slots 42, 43 between adjacent (centermost) staple exit paths so as to be able to cut target tissue between adjacent rows of stapled tissue. The cutting member 40 can be raised or lowered (shown as lowered) a distance in the slots 42, 43 to cut a line between and divide the stapled tissue. The cutting member can be configured to slidably translate straight or pivotably translate upward or downward to be aligned with an axially extending centerline of the stapler head to cut tissue between two adjacent stapled rows of tissue.

Figure 11:
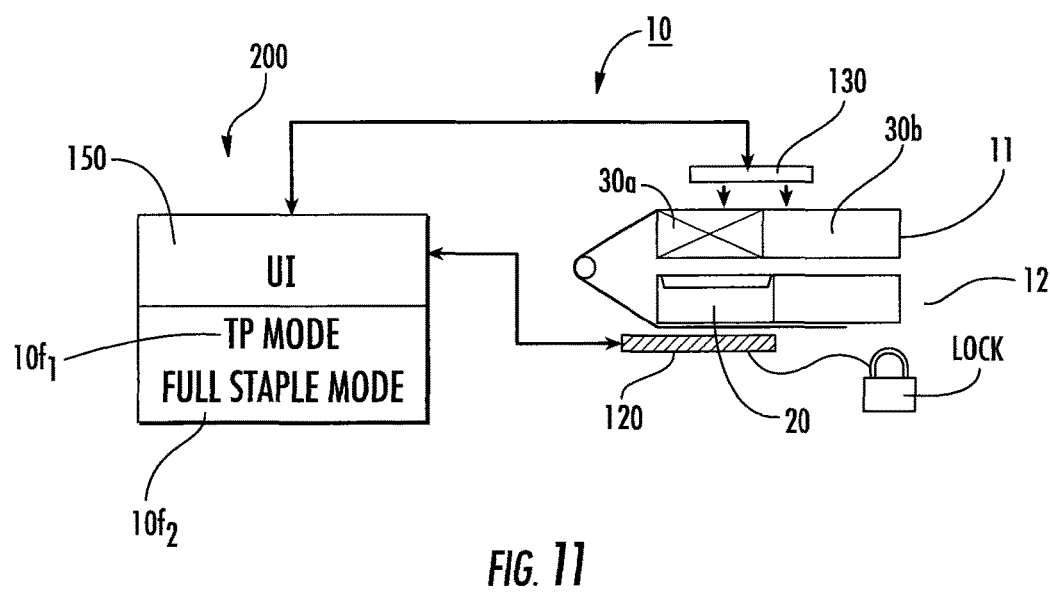
FIG. 11 is a block diagram of a stapler with a control circuit according to embodiments of the present invention.

Referring to FIG. 11, in some embodiments, the stapler 10 can have two different "firing" modes including a tissue protection mode $10f_1$ and a full length staple mode $10f_2$ that can be selectively activated by a user. The stapler 10 can have a control circuit 200 and a User Interface 150 that allows a user to select which mode to use.

In some embodiments, in the tissue protection mode $10f_1$, the tissue protection segment is "active" and the stapler 10 does not discharge staples at the rear portion 30a of the cartridge 30 (only at the forward portion 30b). The partial firing can be carried out in a number of ways. For example, the staple cartridge 30 can "fire" using two different drive mechanisms 130, one for the forward portion and one for the rearward portion. In full length staple mode $10f_2$, the two can fire concurrently to apply staples. In other embodiments, staples can be restrained or blocked from exit paths in the rearward portion while being in communication with the drive or punch mechanism 130 that forces the staples out of the cartridge body. In yet other embodiments, a common punch or drive mechanism 130 can be used to deliver the staples in both portions 30a, 30b, but the punch or drive mechanism can deliver staples from the rearward portion 30a only in the full length staple mode using a linkage or other control or by arranging the staple supply so as to not load the portion 30a in a discharge arrangement for the initial firing $10f_1$ (tissue protection mode). The punch or drive mechanism 130 can be any conventional type including those that are commercially available in one or more of the devices discussed above. The punch or drive mechanism 130 can include, for example, air-driven pneumatic actuators, spring loaded punches, and combinations of same. Some examples of staple drive mechanisms are described in U.S. Pat. Nos. 4,354,628; 5,350,104, 5,655,698; and 7,134, 587, the contents of which are incorporated by reference herein.

In the full length staple mode $10f_2$, staples are applied along substantially the entire length of the cartridge length 30 about the tissue protection segment (when this mode is inactive).

In some embodiments, the stapler 10 can also selectively "lock" the tissue protection segment 20 so that during full staple mode $10f_2$, the tissue protective segment 20 acts as an anvil surface. Thus, in some embodiments, as noted above, the staple cartridge 30 can extend along the entire length of one side of the jaw 11 (shown as top jaw 11, but the cartridge 30 can also be in the bottom jaw 12). A locking member 120 can be inserted under the block 20b or member 20m or about a perimeter of the block 20b or member 20m to deactivate the tissue protection mode to prevent the block 20b from moving downward. Thus, the block 20b or member 20m can define an anvil surface 16 for when the stapler 10 is intended to be operated in a conventional form to form a longer continuous line of staple rows. Where the tissue segment 20 comprises a recess configuration, the stapler 10 can be configured to slidably advance an anvil member to fill or extend across the recess for the "full" firing mode (not shown).

Figure 12A:
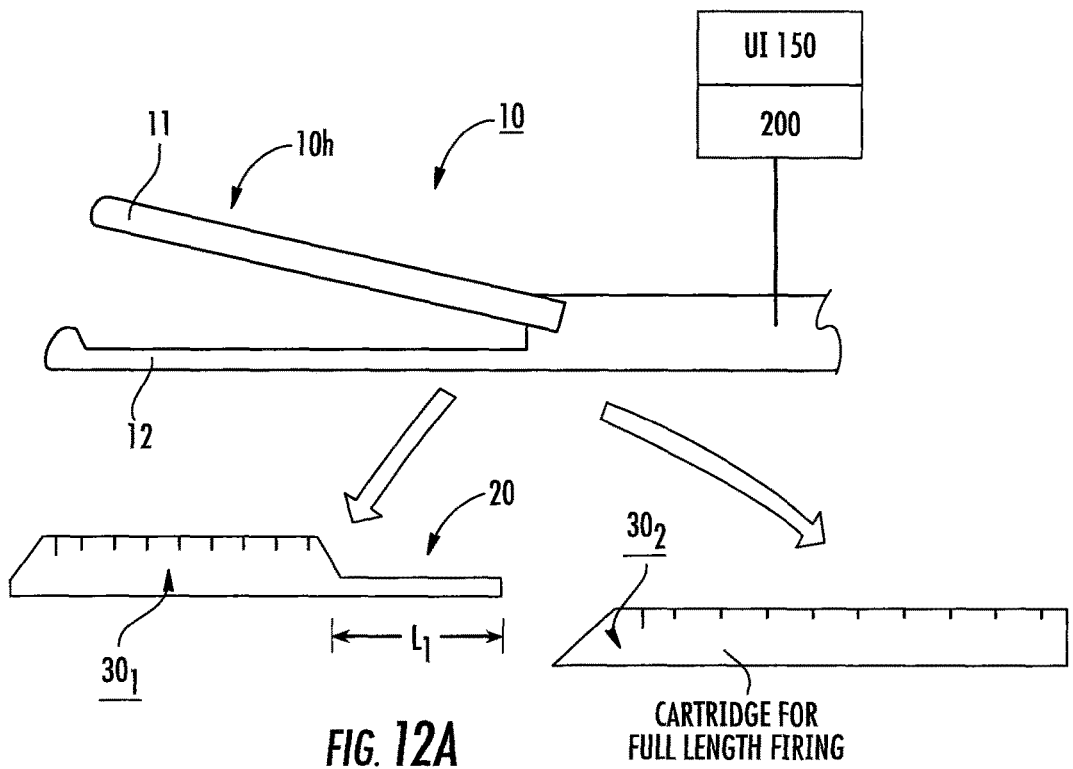
FIGS. 12A-12C are schematic illustrations of a stapler configured to releasably hold two differently configured staple cartridges according to some embodiments of the present invention.
Figure 12B:
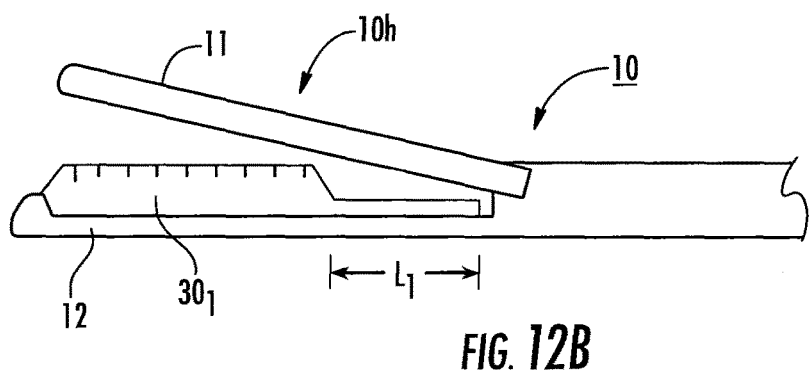
Figure 12C:
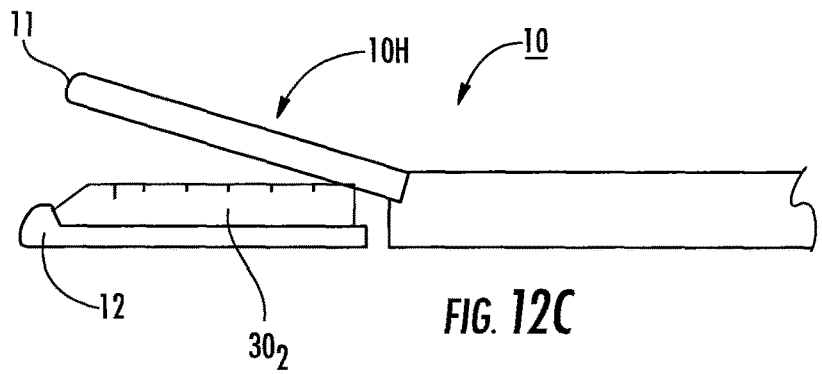

In other embodiments, as shown, for example, in FIGS. 12A-12C, the stapler 10 can be configured to releasably interchangeably hold two differently configured staple cartridges $30_1$, $30_2$. The first cartridge $30_1$ can include the tissue protection segment 20. The second cartridge $30_2$ can include no protection segment or, for example, a smaller tissue protection segment for a longer or "full length" staple delivery mode. Each cartridge $30_1$, $30_2$ can have substantially the same overall length. In some embodiments, one or both of the cartridges $30_1$, $30_2$ can releasably mount to the stapler head using an adapter to help facilitate a suitably tight fit. In other embodiments, the stapler head 10h can each directly interchangeably mount to the stapler head without requiring an adapter. The staple height of the cartridge 30 can vary according to target use. The length of the tissue protection segment 20 (e.g., scallop 20s and/or recess 20r) can also vary according to use as discussed above. In use, in some embodiments, the first cartridge $30_1$ can be mounted to the staple head 10h (e.g., for an initial firing in a GRACE or other procedure) (FIG. 12B). The second stapler cartridge $30_2$ can be a "normal" full length cartridge without the tissue protection segment 20 and can be used in the same stapler head 10h (FIG. 12C) in a cutting or non-cutting mode (e.g., blade or bladeless).

The stapler 10 can include a circuit 200 with a UI 150. The stapler 10 can allow selective cutting (e.g., blade/bladeless) set to occur based on the type of firing mode selected and/or type of cartridge mounted. The circuit 200 can be configured with a safety monitoring circuit that generates an alert if a cutting mode is selected and is not compatible with the cartridge loaded and/or firing mode selected.

The circuit 200 can accept user input via UI 150 to identify the type of cartridge $30_1$, $30_2$ mounted on the stapler. Alternatively or additionally, the circuit 200 can include an on-board identifier circuit that electronically identifies the type of cartridge loaded (e.g., different resistor values, different mounting connections and the like) so that the stapler 10 is "smart" and can determined which firing mode and/or which cutting mode to use based on which cartridge $30_1$, $30_2$ is loaded. The circuit 200 can optionally automatically and/or electronically block cutting (e.g., operate on a presumption of bladeless firing) if the full length cartridge $30_1$ is mounted and/or for safety to require a user to select or confirm a cutting mode or override a default of not cutting, to confirm cutting is desired for a particular firing and/or procedure.

The circuit 200 can include a digital signal processor and/or an Application Specific Integrated Circuit (ASIC) (e.g., ASIC and/or processor with software) that includes or executes part or all of the computer readable program code for generating the "firing" and subsequent cutting (when the jaws are locked against each other). The on-board circuit 200 can include sensors and timers so that the cutting can be automatically carried out in a very accurate manner to cut only the stapled tissue after the rows of staples are applied to tissue, such as when a partial (tissue protection mode) is engaged.

Where the stapler has a selectively operable tissue protection mode $10f_1$, the circuit 200 may be configured to activate the locking member 120 after an initial firing, automatically when "full length" firing is selected $10f_2$, for example upon User Input. The circuit 200 can include a data processing system which may, for example, be incorporated or integrated into a processor.

Figure 13:
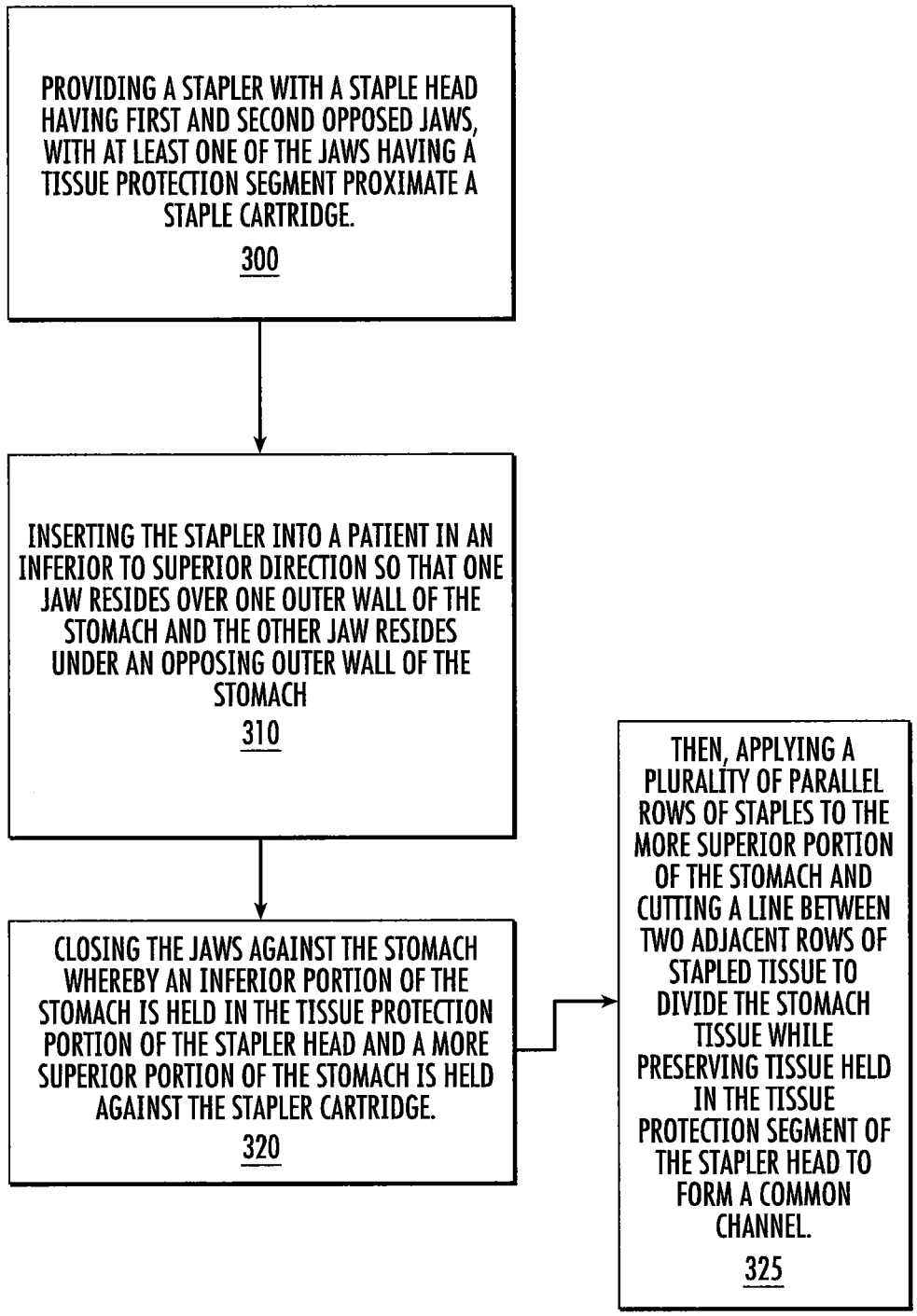
FIG. 13 is a flow chart of exemplary steps that can be used to carry out some methods of the present invention.

FIG. 13 is a flow chart of exemplary steps that can be used to carry out embodiments of the present invention (such as associated with a GRACE procedure). A stapler is provided with a staple head having first and second opposed jaws, with at least one of the jaws having a tissue protection segment proximate a staple cartridge (block 300). The stapler is inserted into a patient in an inferior to superior direction so that one jaw resides over one outer wall of the stomach and the other jaw resides under an opposing outer wall of the stomach (block 310). The jaws are closed against the stomach whereby an inferior portion of the stomach is held in the tissue protection portion of the stapler head and a more superior portion of the stomach is held against the stapler cartridge (block 320). Then, a plurality of parallel rows of staples are applied to the more superior portion of the stomach and a line between two adjacent rows of stapled tissue is cut to divide the stomach tissue while preserving tissue held in the tissue protection segment of the stapler head to form a common channel (block 325). This forms an opening (typically oval or oblong) through the stomach with a stapled perimeter of tissue. A lower portion of this stapled tissue of this opening will form part of a base portion of a neo-esophagus or a junction with the common channel (FIG. 1).

Embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a programmed digital signal processor or microcontroller.

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer, stapler with an on-board circuit or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 14:
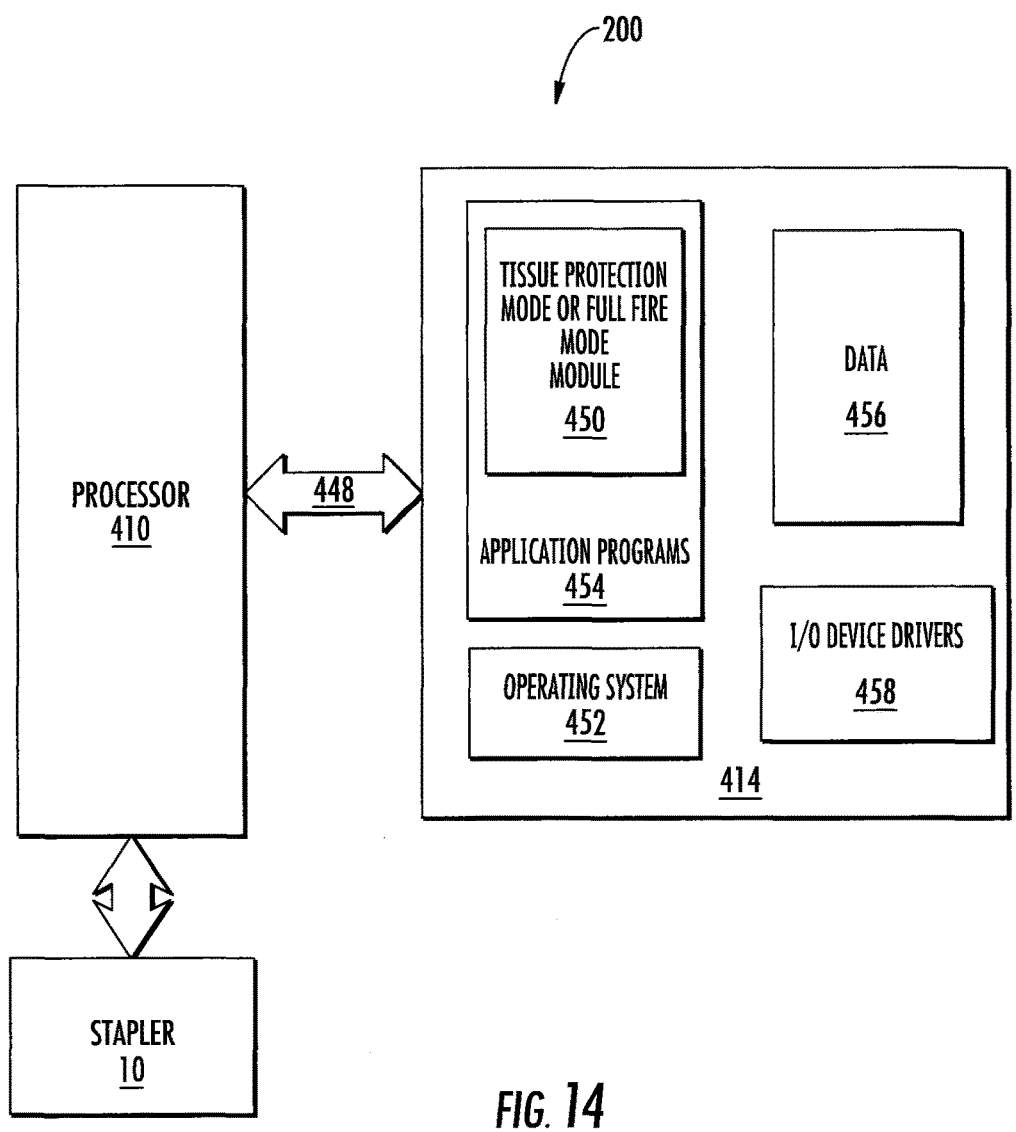
FIG. 14 is a block diagram of a circuit/data processing system according to embodiments of the present invention.

FIG. 14 is a schematic illustration of a portion of a circuit 200 that can be used with or forms part of the stapler 10. The circuits and/or data processing systems may be incorporated in a digital signal processor in any suitable device or devices. As shown in FIG. 14, the processor 410 communicates with a stapler 10 and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

As shown in FIG. 14, the memory 414 may include several categories of software and data used in the data processing system: the operating system 452; the application programs 454; the input/output (I/O) device drivers 458; and data 456. The data 456 can include sensor synchronization or timing data for timing the firing of the stapler or the timing of the cutting action (where used) after stapling is completed. The data 456 can include electronic identifiers to recognize which cartridge is loaded (where more than one type is used such as shown in FIGS. 12A-12C). The data 456 can include defined operational features to promote safe use of the stapler, such as monitoring for use of a limited cutting mode when the tissue protection mode or segment is in use.

As will be appreciated by those of skill in the art, the operating systems 452 may be any operating system suitable for use in rapid data processing, including, but not limited to those from Microsoft, Inc. (Windows), Apple Computer, Inc. (MacOS), Wind River (VxWorks), RedHat (Linux), LabView or proprietary operating systems. The I/O device drivers 458 typically include software routines accessed through the operating system 452 by the application programs 454 to communicate with devices such as I/O data port(s), data storage 456 and certain memory 414 components. The application programs 454 are illustrative of the programs that implement the various features of the circuit (e.g., data processing system) and can include at least one application, which supports operations according to embodiments of the present invention. The circuit can include a Tissue Protection Mode and Full Firing Mode Module 450. Finally, the data 456 represents the static and dynamic data used by the application programs 454, the operating system 452, the I/O device drivers 458, and other software programs that may reside in the memory 414.

While the present invention is illustrated, for example, with reference to the Module 450 being application programs in FIG. 14, as will be appreciated by those of skill in the art, other configurations may also be utilized while still benefiting from the teachings of the present invention. For example, the Module 450 and/or may also be incorporated into the operating system 452, the I/O device drivers 458 or other such logical division of the data processing system. Thus, the present invention should not be construed as limited to the configuration of FIG. 14 which is intended to encompass any configuration capable of carrying out the operations described herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A gastrointestinal treatment method, comprising:
providing a stapler with a staple head having first and second opposed jaws, with at least one of the jaws having a tissue protection segment proximate a staple cartridge;
inserting the stapler into a patient in an inferior to superior direction so that one jaw resides over one outer wall of the stomach and the other jaw resides under an opposing outer wall of the stomach;
closing the jaws against the stomach whereby an inferior portion of the stomach is held in the tissue protection portion of the stapler head and a more superior portion of the stomach is held against the stapler cartridge, wherein tissue held against the tissue protection segment is protected from undue injury; then
applying a plurality of parallel rows of staples to only the more superior portion of the stomach and not to tissue held in the tissue protection segment of the stapler jaws; and
cutting between two adjacent rows of stapled tissue to divide the stomach tissue.

2. The method of claim 1, wherein the applying and cutting steps are carried out to form a first opening through the stomach with a stapled perimeter of tissue.

3. The method of claim 2, further comprising:
applying staples to additional tissue above the first opening in a length sufficient to reach a junction of a natural esophagus at an upper portion of the stomach; and
cutting the additional stapled tissue to form a neo-esophagus.

4. The method of claim 2, further comprising using a lower portion of the stapled tissue of the first opening to form part of a base portion of a neo-esophagus and/or an upper wall of a junction merging with a common channel.

5. A method of applying staples to a limited region of tissue, comprising:
inserting a surgical stapler into a patient, the surgical stapler having first and second cooperating opposed jaws;
closing the jaws about a target region of tissue; then
applying a plurality of rows of staples to a first sub-portion of tissue held between the jaws while protecting a second sub-portion of tissue from compressive injury; and
cutting between two adjacent parallel rows of applied staples to form an opening with a stapled perimeter of divided tissue that is spaced apart from but proximate to the second sub-portion of tissue.

6. The method of claim 5, wherein the target tissue is stomach tissue.

7. The method of claim 5, wherein the target tissue is esophageal tissue.

* * * * *